United States Patent [19]
Losee et al.

[11] Patent Number: 4,563,331
[45] Date of Patent: Jan. 7, 1986

[54] SYSTEM FOR MEASURING BIOLUMINESCENCE FLASH KINETICS

[75] Inventors: Jon R. Losee; David Lapota, both of San Diego, Calif.

[73] Assignee: The United States of America as represented by the Secretary of the Navy, Washington, D.C.

[21] Appl. No.: 553,656

[22] Filed: Nov. 21, 1983

[51] Int. Cl.[4] .................. G01N 21/62; G01N 21/70
[52] U.S. Cl. .................. 422/52; 250/361 C; 356/244; 356/417; 435/291; 435/311; 435/808; 436/172
[58] Field of Search .................. 356/244, 417; 250/361 C, 461.2, 461.1; 422/52, 68; 436/172; 435/8, 288, 291, 828, 311

[56] References Cited
U.S. PATENT DOCUMENTS

| | | | |
|---|---|---|---|
| 3,489,498 | 1/1970 | Brody et al. | 356/417 |
| 3,579,306 | 5/1971 | Crone | 356/244 |
| 3,710,107 | 1/1973 | Warren et al. | 436/172 |
| 3,726,599 | 4/1973 | Neary | 422/52 |
| 3,797,999 | 3/1974 | Witz et al. | 422/52 |
| 3,849,653 | 11/1974 | Sakaide et al. | 436/172 |
| 3,979,181 | 9/1976 | Plakas | 422/52 |
| 4,099,920 | 7/1978 | Huss | 422/52 |
| 4,213,703 | 7/1980 | Haunold et al. | 250/361 C |
| 4,236,895 | 12/1980 | Stahl | 436/172 |
| 4,238,198 | 12/1980 | Swaim et al. | 422/52 |
| 4,303,410 | 12/1981 | Copeland | 436/172 |
| 4,472,352 | 9/1984 | Quesneau et al. | 422/52 |

OTHER PUBLICATIONS

Tett et al., "Marine Bioluminescence", *Oceanogr. Mar. Biol. Ann. Rev.*, 1973, 11, 89–173.
Clarke et al., "Comparative Studies of Luminescence in Copepods and Other Pelagic Marine Animals", *J. Mar. Biol. Ass. U.K.*, (1962), 42, 541–564.
Hardy et al., "Experimental Studies of Plankton Luminescence", *J. Mar. Biol. Ass. U.K.*, (1964), 44, 435–484.

*Primary Examiner*—Arnold Turk
*Attorney, Agent, or Firm*—R. F. Beers; E. F. Johnston; Harvey Fendelman

[57] ABSTRACT

A test chamber is disclosed for determining the bioluminescent signatures of planktonic organisms in which a light tight chamber has at least one light port, and preferably two light ports, where photomultiplier tubes are connected to the test chamber for detecting and measuring the flash kinetics of marine organisms. A door is pivotally mounted on the light tight chamber for permitting insertion and withdrawal of an organism sample holder. A vacuum tube is connected to the test chamber and to the sample holder via a passageway such that the organism can be excited by means of drawing off the fluid containing the organism. The bioluminescent characteristics of the organisms in the sample holder can then be detected and measured by means of the photomultiplier tubes. Preferably, a third port is provided on the test chamber where, alternatively, a third multiplier tube may be connected, or one of the two photomultiplier tubes can be connected with a different orientation with respect to the sample holder, or a light tight diaphragm may be placed across the third light port such that chemical irritants may be injected into the sample holder by means of a syringe through the light tight diaphragm without permitting the entry of light into the test chamber. The outputs of the photomultiplier tubes may be used to measure the instantaneous intensity of the bioluminescent flashes of the organisms. The collected data may be recorded to help identify which organisms are responsible for the measured bioluminescence in the surface waters of the worlds oceans.

15 Claims, 5 Drawing Figures

SYSTEM FOR MEASURING BIOLUMINESCENCE FLASH KINETICS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates generally to the field of detecting and measuring bioluminescence of organisms and, more particularly, to the field of detecting and measuring bioluminescent signatures of planktonic organisms.

Bioluminescence has been observed at one time or another in most oceans of the world. In fact, some oceans are known for brillant surface displays which are observed on a year-round basis. While these qualtitative observations have been noted and compiled from frequently traveled areas, there have been relatively few studies describing the specific causative organisms responsible for the observed display. In some instances, the species responsible for bioluminescence has not been determined due to inadequate sampling procedures or unavailable equipment.

A major problem which marine scientists face when conducting bioluminescence measurements at sea is correlating collected photoplankton and zooplankton samples with either measured or visually observed bioluminescence. Determination of which of the collected organisms are luminescent has either been made visually while onboard ship or by reviewing published reports of these species. Both methods appear to be inadequate since some luminous species may not flash or may flash at a level not visually observable when agitated following collection procedures. The literature accounts of which species of organisms are luminescent are quite incomplete. To compound this problem, some bioluminescent forms, such as dinoflagellates, collected from one geographic area have not been observed to be luminescent when collected from other areas.

The use of plankton chambers for the photoelectric recording of flash responses from luminescent dinoflagellates has been reported in literature. See for instance P. B. Tett and M. G. Kelly, 1973, "Marine Bioluminescence" in volume 11, pages 89 through 173 of *Oceanography and Marine Biology Annual Review* and also A. C. Hardy and R. H. Kay, 1964, "Experimental Studies of Plankton Luminescence" in volume 44, pages 435 through 486 of the *Journal of Marine Biology Association United Kingdom*. Further, vacuum triggered or induced flash responses have reportedly been observed but apparently this method of stimulation has not been investigated in any great detail. See, for instance, G. L. Clark, R. J. Conover, C. N. David, and J. A. C. Nicol, 1962, "Comparative Studies of Luminescence in Copepods and Other Pelagic Marine Animals" in volume 42, pages 541 to 564 of the *Journal of Marine Biology Association United Kingdom*.

SUMMARY OF THE INVENTION

To facilitate observations of planktonic organism bioluminescence, the laboratory plankton test chamber of the present invention was built to measure bioluminescence from individual dinoflagellate cells and zooplankters recently isolated from fresh net collections.

The present invention has the following immediate advantages over prior art techniques. Relatively large numbers of isolated organisms can be tested on a daily basis either during photophase or scotophase. Organisms can be tested individually for assessment of probable luminescence contributing to the measured surface bioluminescence. Also, confirmation of bioluminescence in known luminous organisms as well as observing bioluminescence in plankters not previously known to be luminescence is achievable with the present invention.

In accordance with the present invention, freshly collected plankton samples are diluted with filtered seawater to facilitate isolation of the desired test organism. The isolated organisms are placed into quartz sample holders with approximately 10 ml of filtered seawater. The lucite base of the sample holders is drilled to accommodate vacuum suction. Whatman GF/C filter paper lines the bottoms of the sample holders and retains the test organism when water is removed by the vacuum. This "drawing off" effect appears to be sufficient to consistently stimulate luminescence from potentially luminous organisms which are tested. It has been discovered that the present technique not only works well for copepods, but also for dinoflagellates and larval and adult euphausiids, ostracods, larvaceans, and small siphonophores. The organism under test can be re-wetted while still in the test chamber by injecting seawater or possibly other irritants through an unused light tight port. In some instances, significant responses are obtained upon re-wetting and re-drying of the organisms.

In order to observe the luminescence from the vacuum stimulated organisms under test, two photomultiplier tubes are mounted on the two other test chamber ports. One photomultiplier tube measures the broadband (e.g. 350–650 nm wavelengths) intensity while the other photomultiplier tube measures near ultraviolet light from the induced flash (wavelengths $<400$ nm). Filters are affixed near the surface of the photocathode of the photomultiplier tube to accommodate measurements in the near ultraviolet region. Both photomultiplier tubes are used in a single photon count mode with their signal pulses fed to multichannel analyzers operating in the multiscaler mode. Coincident signals may be obtained by synchronizing the analyzers with a common start pulse. The output of each photomultiplier tube may be displayed as a time sequence of counts/time bin for the induced flash from the organism. Time resolution from each analyzer channel (time bin size) may be, for instance, $10\mu$ sec to 1 sec, switch selectable. Typical channel resolution is set, for instance, at 1, 4, 10, and 40 msec for a total of 1022 channels available. The instantaneous intensity of the signal is proportional to the number of counts in each channel. From the displayed data, rise time and duration of the flash can be examined coincidentally for both the broadband and ultraviolet spectral regions. These data may then be recorded on a digital cassette recorder.

OBJECTS OF THE INVENTION

Accordingly, it is a primary object of the present invention to disclose a novel test system for determining bioluminescent characteristics of organisms which can accommodate relatively large numbers of isolated organisms either during photophase or scotophase.

It is a further object of the present invention to disclose a test chamber for detecting and measuring bioluminescence of individual organisms.

It is still a further object of the present invention to disclose a test chamber which is extremely useful for confirmation of bioluminescence in known luminous organisms as well as observing bioluminescence in plankters not previously known to be luminescent.

These and other objects of the invention will become more readily apparent from the ensuing specification when taken together with the drawings.

DESCRIPTION OF THE PREFERRED EMBODIMENT

Figure 1:
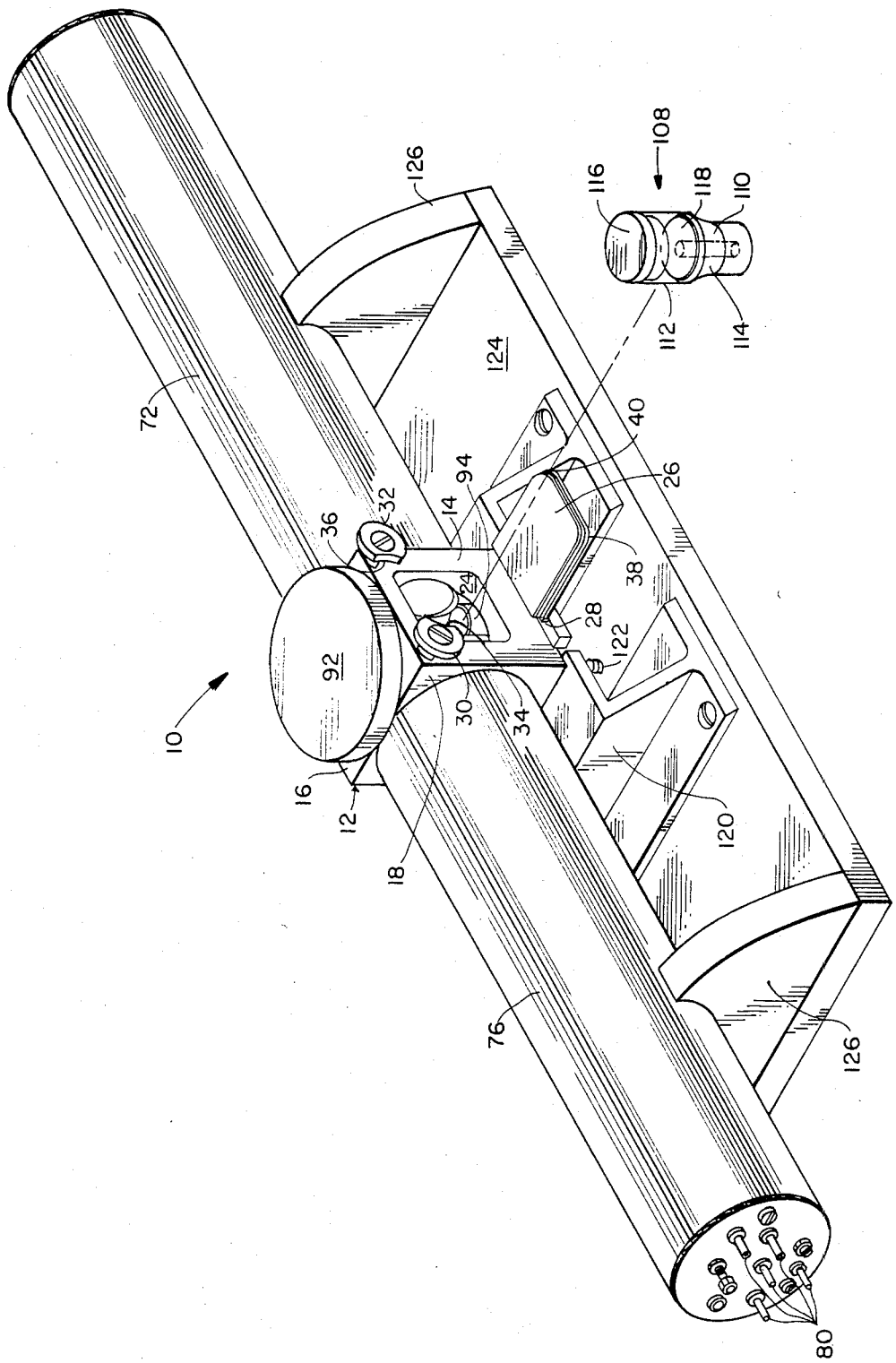
FIG. 1 is an isometric view of the bioluminescent test chamber of the present invention.

Referring now to FIGS. 1 through 5 collectively, the test chamber of the present invention will be described.

The test chamber 10 of the present invention includes a light tight test chamber 12 as its central portion. Test chamber 12 is formed generally in the shape of a hollow cube having a front surface 14, a top surface 16, side surfaces 18 and 20 respectively, side 20 being illustrated in FIG. 2, bottom surface 22, illustrated in FIG. 3, and a rear surface (not shown). Interior cavity 24 of the chamber 12 is closed off by door 26 which is attached to the chamber 12 by means of hinge mechanism 28. Thus, the interior chamber 24 can be sealed by closing door 26 and securing it in the closed position by means of rotatable latch mechanisms 30 and 32. It is noted that latch mechanisms 30 and 32 both contain contoured portions 34 and 36 for permitting the corners 38 and 40, respectively of door 26 to pass by them as the door is being closed. Once the door 26 is positioned in the closed position sealing the cavity 24, the latch mechanisms 30 and 32 may be rotated in either direction to secure the door.

Figure 4:
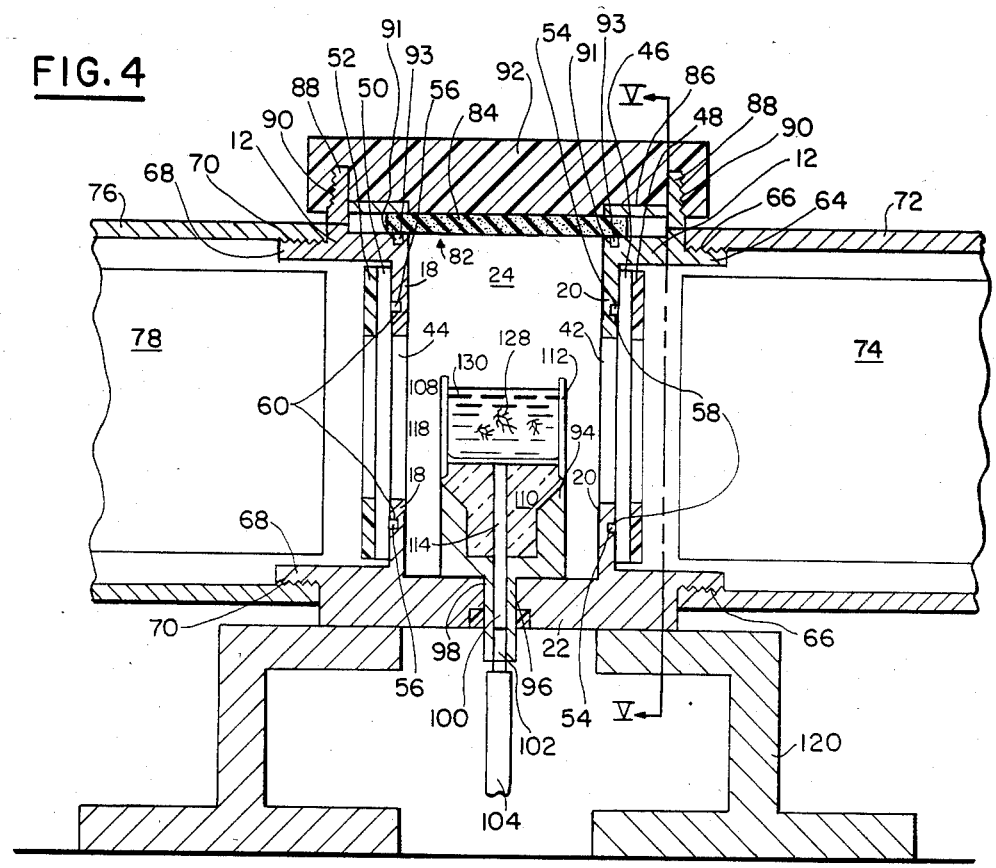
FIG. 4 is a front view cross-section of the test chamber of the present invention.
Figure 5:
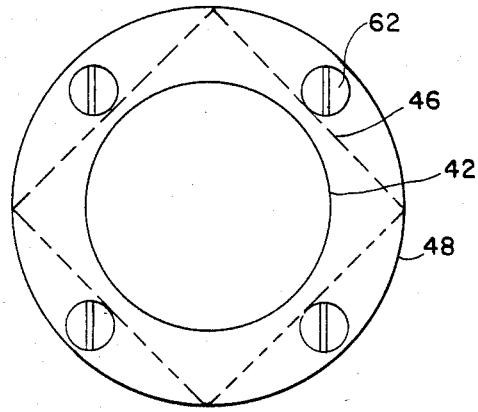
FIG. 5 is a partial end view cross-section of the test chamber of the present invention.

Referring to FIG. 4 it can be seen that the chamber 12 has a circular shaped aperture 42 formed in side wall 20 and a similar circularly shaped aperture 44 formed in side wall 18. A first optical filter 46 is placed over the aperture 42 and is secured in position by means of retaining ring 48. Similarly, on side 18 of test chamber 12 a second filter 50 is placed over aperture 44 in side wall 18 and is secured in place by means of retaining ring 52. O-rings 54 and 56 are fitted into the grooves 58 and 60, respectively formed in side walls 20 and 18 respectively. O-rings 54 and 56 ensure that there is a light tight seal between the filters 46 and 50 and their respective side walls 20 and 18. The retaining rings 48 and 52 are secured to the side walls 20 and 18, respectively by means of screws or other suitable mechanisms 62. As can be seen in FIG. 5, the filters 46 and 50, which are identical in shape, may be square shaped filters having sides which are longer than the diameter of apertures 42 and 44 such that they completely cover those apertures and may be positioned relative to the retaining rings 48 and 52 as illustrated to accommodate the screws 62, which screw into side walls 18 and 20 (not shown).

A cylindrically shaped flange member 64 extends outward from sidewall 20 and has an exterior threaded surface 66. Similarly, a cylindrically shaped flange member 68 extends outwardly from side wall 18 and has an exterior threaded surface 70. A cylindrically shaped photomultiplier tube housing 72 contains photomultiplier tube assembly 74 and has an interior threaded surface on its left end which mates with threaded surface 66 as is illustrated in FIG. 4. Photomultiplier tube assembly 74 is thus in position to be irradiated by any light which passes through aperture 42 in the test chamber 12 and through filter 46. Similarly, at the left end of the device as illustrated in FIGS. 1 and 4, cylindrically shaped photomultiplier tube housing 76 has an interior threaded surface at its right end which mates with the threaded surface 70 on flange 68. Photomultiplier tube housing 76 contains photomultiplier tube assembly 78 which is positioned to be irradiated by light passing through aperture 44 and filter 50. It is noted that in the preferred embodiment of the present invention, filters 46 and 50 filter different frequency ranges of light, for instance, filter 46 being designed such that photomultiplier tube assembly 74 is irradiated with a broadband spectrum of light and such that, for example, filter 50 filters light such that photomultiplier tube 78 is irradiated with the ultraviolet spectrum of light. The ends of photomultiplier tube housings 72 and 76 are provided with appropriate electrical connections such as BNC connectors generally illustrated as item 80 which are connected to the photomultiplier tube assembly 74 and 78, respectively within the interiors of the housings 72 and 76 as would be readily understood by one of ordinary skill in this art.

The top surface 16 of test chamber 12 has an aperture 82 similar to apertures 42 and 44 in the side walls 18 and 20, respectively. A light tight diaphragm 84 covers aperture 82 and the top surface 16 and is preferably formed of neoprene rubber which is a material that will permit the needle of a syringe to be passed through it while maintaining a light tight closure around the needle and while maintaining a light tight seal across the aperture 82. The diaphragm 84 is held in place by retainer ring 86 which is secured to the test chamber 12 by means of screws (not shown) in an arrangement similar to that illustrated with respect to the filters 46 and 50 illustrated in FIG. 5. Cylindrically shaped flange member 88 extends from the top surface 16 of the test chamber 12 and has an exterior threaded surface 90. When the diaphragm 84 is not in use and when the port 82 of the test chamber 12 is not in use, generally disc shaped cap member 92 closes the port 82 in a light tight fit. It is noted that the flange 88 is identical in size and dimension to the flanges 64 and 68 such that either the photomultiplier tube housing and photomultiplier tube 72, 74 or the photomultiplier tube housing and photomultiplier tube 76, 78 may be removed from its respective position illustrated in FIG. 4 and screwed onto the flange member 88. In this manner, the photomultiplier tube assembly 74 or 78 may be reoriented with respect to the organism samples which are placed within the interior 24 of the chamber 12.

Figure 2:
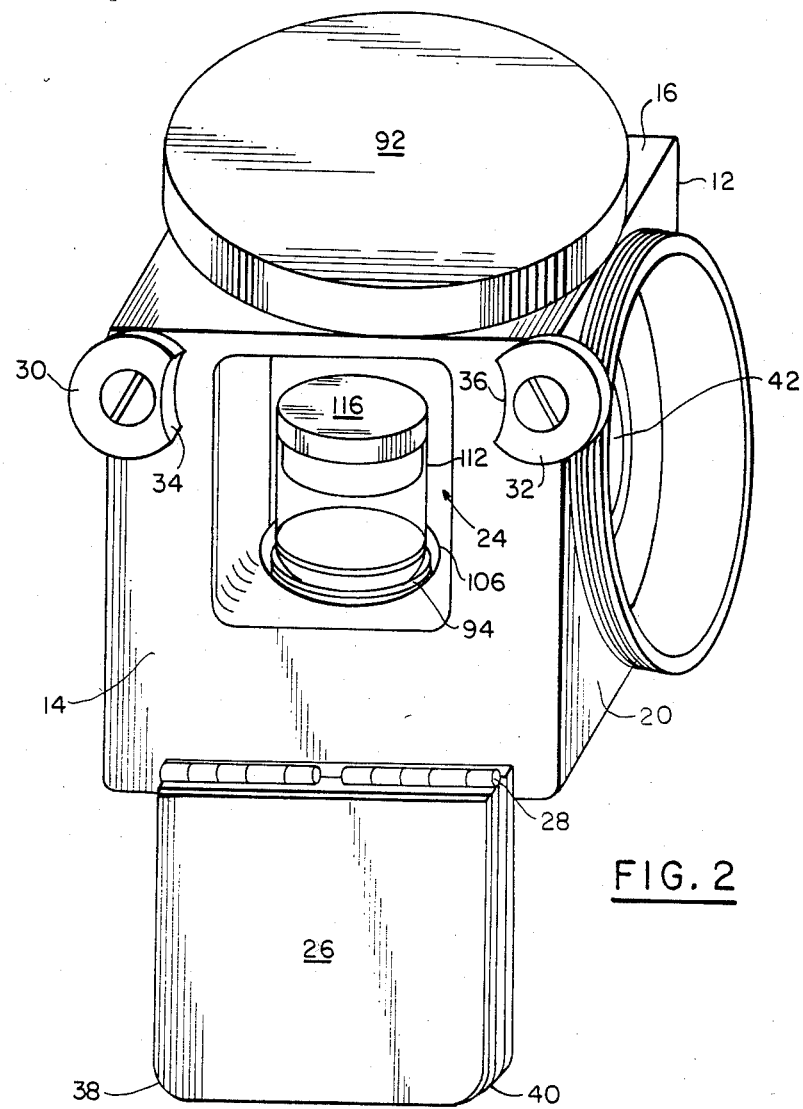
FIG. 2 is an isometric view of the test chamber of the present invention with the photomultiplier tubes removed and with the front door open illustrating the sample holder in place within the test chamber.
Figure 3:
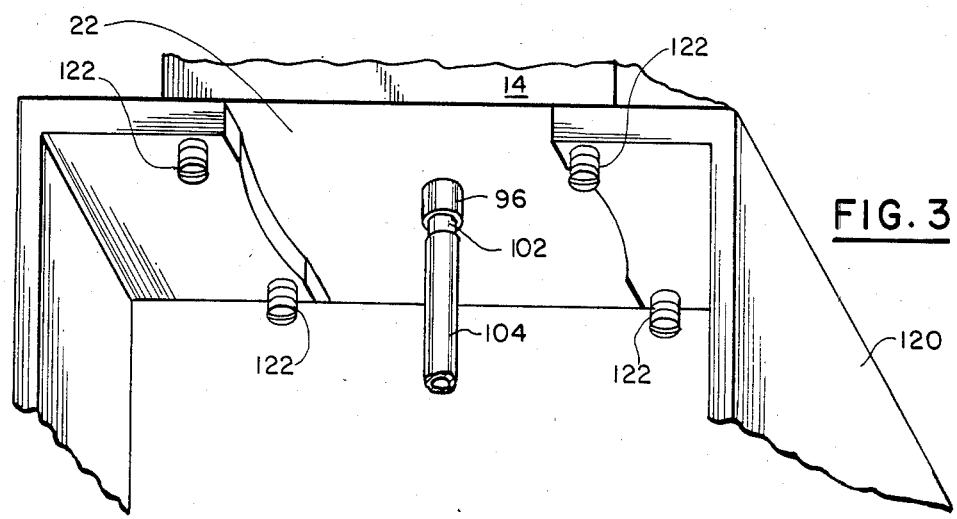
FIG. 3 is an isometric view of the bottom portion of the test chamber of the present invention illustrating the vacuum line.

Within the interior compartment 24 of the test chamber 12, a sample holder support fixture 94 is secured to the base 22 of the test chamber and includes a tube shaped portion 96 which extends through the passageway 98 formed in the bottom 22 of the chamber. It can be seen that the tube portion 96 has an interior passageway 100 into which a short section of tube 102 is fitted. Connected to the short section of tube 102 is a section of vacuum tubing 104 to which a vacuum pump or the like is connected (not shown). As illustrated in FIG. 2 the sample holder support fixture 94 may be positioned within a recessed area 106 formed within the bottom 22 of the test chamber 12. It is noted that, for purposes of simplicity, the recessed area 106 is not illustrated in FIG. 4.

An organism sample holder 108 has a base member 110 preferably formed of lucite and has a top cylindrical portion 112 preferably formed of quartz material. The base portion 110 of the sample holder 108 has a passageway 114 that aligns with the passageway 100 formed in the sample holder support fixture 94. The sample holder 108 also includes a removable cap 116 for closing off the holder, if desired. A filter disc 118 lines the bottom of the cylindrical portion 112 of the sample holder 108 and functions to retain the test organism following water removal to be described. Alternatively, or in addition to the filter disc 118, the top of the base portion 110 of the sample holder 108 may include a disc shaped portion of scintered glass. As can be seen in FIG. 4, the sample holder 108 fits in a male-female relationship into the sample holder support fixture 94. By utilization of a tweezer type mechanism having curved arms to accommodate the cylindrical portion 112 of the sample holder 108, the sample holder 108 may be inserted into and withdrawn from the cavity 24 of the test chamber 12.

The test chamber 12 with its connected photomultiplier tubes and tube housings 74, 78, 72 and 76, respectively are mounted on chamber stand 120 and attached to the stand 120 by means of screws of 122 or other suitable means. For further support, the chamber stand 120 may be screwed to base support 124 which includes support sections 126 which are formed as illustrated in FIG. 1 for providing additional support to the photomultiplier tube housing 72 and 76.

In order to observe the luminescence from collected organisms, the organisms 128 are collected with approximately 6 ml of filtered seawater and placed in the sample holder 108. The cap 116 of the sample holder 108 is positioned in place and the sample holder 108 containing the filtered seawater and organism samples 128 is placed by means of the tweezer type mechanism previously described into the interior cavity 24 of the test chamber 12 and fitted into the sample holder support fixture 94 as is illustrated in FIG. 4. The latch mechanisms 32 and 34 are rotated to the position illustrated in FIG. 2 such that the door 26 of the test chamber 12 may be closed. Once closed, the latch mechanisms 30 and 32 are rotated to secure the door from opening and to form an air tight, light tight sealed compartment 24 within the interior of the test chamber 12. Next, the water 130 within the sample holder 108 is drawn off by means of connecting a vacuum pump (not shown) to the vacuum line 104. When the pump is turned on, the water is removed by the vacuum. This "drawing off" effect has been observed to be sufficient to consistently stimulate luminescence from the potentially luminous organisms 128 which are being tested. The luminescence of the organisms 128 irradiates the photomultiplier tube assemblies 74 and 76 which output electrical signals indicative of the intensity of the luminescence of the organisms 128. The photomultiplier tube assemblies 74 and 78 which may, for instance, be RCA model 8575 photomultiplier tubes, may be used in a single photon count mode with their signal pulses fed to, for instance, two Davidson multichannel analyzers operating in the multiscaler mode. Coincident signals may be obtained by synchronizing the analyzers with a common start pulse. The output of each photomultiplier tube assembly 74 at 78 may be displayed as a time sequence of counts/time bin from the induced flash from the organisms 128. Time resolution of each analyzer channel (time bin size) may be $10\mu$ sec to 1 sec, switch selectable. Typical channel resolution may be set at 1, 4, 10, and 40 msec, for a total of 1022 channels available. In this manner, the displayed data indicates rise time and duration of the flash and these characteristics may then be examined coincidentally for both light frequency ranges detected by the photomultiplier tube assemblies 74 and 78. The data may then be recorded on a digital cassette recorder or charted on a graph.

It can be seen in FIG. 4 that the photomultiplier tube assemblies 74 and 78 are aligned such that their longitudinal axes are generally colinear. Alternatively, either the photomultiplier tube assembly 74 with its associated housing 72 or the photomultiplier tube assembly 78 with its associated housing 76 may be removed from its position as illustrated in FIG. 4 and may be attached to the flange 88 on the top of the test chamber 12 such that the two photomultiplier tube assemblies 74 and 78 would then be in generally orthogonal relationship. This alternative mode of operation permits luminescence data collection from a different perspective. It is noted that in this alternate mode of operation the cap member 92 and the diaphragm 84 would be removed and not utilized.

In a further alternate mode of operation of the present invention, the photomultiplier tube assemblies 74 and 78 and their associated housings 72 and 76, respectively, are utilized in the position illustrated in FIG. 4. However, in this alternate mode of operation, the cap member 92 is removed and the diaphragm 84 is retained in place. With the diaphragm 84 in place, a light tight seal is retained across aperture 82 in the top surface 16 of the test chamber. Organisms may be collected in a volume of seawater and placed into the sample holder which is then placed into the chamber 12 as described above, and the door 26 is then latched closed. The needle of a syringe containing a stimulant or irritant such as acid or alcohol may then be inserted into the diaphragm 94. This action of injecting stimulants or irritants by means of a syringe into the sample holder 108 through diaphragm 84 is sufficient to excite the organisms to luminescence. This luminescence may then be observed in the same manner as previously described with regard to removal and insertion of the sample holder 108.

Obviously, many modifications and variations of the present invention are possible in the light of the above teachings. It is therefore to be understood that within the scope of the appended claims the invention may be practiced otherwise than as specifically described.

What is claimed is:

1. A test chamber for determining bioluminescent signatures of organisms comprising:
   a light tight test chamber having a first light port in a first surface thereof, having a doorway in a second surface thereof and having a chamber base;
   a door pivotally mounted on said light tight chamber having opened and closed positions and covering said doorway when in said closed position;

a sample holder support fixture secured to said chamber base within the interior of said test chamber, having a passageway extending from the interior of said test chamber to the exterior of said test chamber;

an organism sample holder removably positioned within said sample holder support fixture and being removable to the exterior of said test chamber, having a top portion and a base portion, said base portion having a passageway extending at one end through said base portion for alignment with said sample holder support fixture passageway and extending at its other end to said top portion;

means positioned within said sample holder top portion and covering said base portion passageway for preventing said organisms from entering said passageway while permitting fluids containing the organisms to be drawn into said passageway;

first light detecting means secured to said light tight chamber adjacent said first light port for providing an electrical output when irradiated by light, emitted from said organisms, passing through said first light port.

2. The test chamber of claim 1 further comprising:
a second light port in a second surface of said test chamber; and
second light detecting means secured to said light tight chamber adjacent said second light port for providing an electrical output when irradiated by light, emitted from said organisms, passing through said second light port.

3. The test chamber of claim 2 wherein said first and second light detecting means each comprise photomultiplier tubes.

4. The test chamber of claim 3 wherein:
said first light detecting means comprises a first light filter, for filtering light within a first range of frequencies, positioned between said first photomultiplier tube and said first light port; and
said second light detecting means comprises a second filter, for filtering light within a second range of frequencies, positioned between said second photomultiplier tube and said second light port.

5. The test chamber of claim 2 further comprising:
an additional port in a third surface of said test chamber.

6. The test chamber of claim 5 further comprising:
light tight diaphragm means for covering said additional port and for enabling the injection of chemical irritants via a syringe into said sample holder.

7. The test chamber of claim 6 wherein:
said light tight diaphragm means comprises neoprene rubber.

8. The test chamber of claim 1 wherein:
said sample holder top portion is a cylindrical shaped member comprised of quartz.

9. The test chamber of claim 8 wherein:
said sample holder base portion comprises a plastic member that joins with said sample holder support fixture in a male-female relationship.

10. The test chamber of claim 1 further comprising:
hinge means secured to said light tight chamber and to said door for enabling said door to pivot between said open and closed positions.

11. The test chamber of claim 10 further comprising:
latch means secured to said light tight chamber for latching said door in a closed position.

12. The test chamber of claim 1 wherein:
said preventing means comprises filter paper.

13. The test chamber of claim 3 wherein:
said first and second light ports are on opposite surfaces of said light tight chamber; and
said first and second light detecting means photomultiplier tubes have longitudinal axes that are approximately colinear.

14. The test chamber of claim 1 further comprising:
a test chamber stand for supporting said test chamber.

15. The test chamber of claim 1 further comprising:
a vacuum line coupled to said sample holder support fixture passageway.

* * * * *